United States Patent
Park

(10) Patent No.: US 6,351,132 B1
(45) Date of Patent: Feb. 26, 2002

(54) MISCIBLE LIQUID CAPACITIVE SENSING SYSTEM

(75) Inventor: Kyong M. Park, Thousand Oaks, CA (US)

(73) Assignee: Kavlico Corporation, Moorpark, CA (US)

(*) Notice: Subject to any disclaimer, the term of this patent is extended or adjusted under 35 U.S.C. 154(b) by 0 days.

(21) Appl. No.: 09/389,703

(22) Filed: Sep. 3, 1999

(51) Int. Cl.[7] ............................................. G01R 27/26
(52) U.S. Cl. ..................... 324/664; 324/665; 324/666
(58) Field of Search ............................. 324/664, 676, 324/677, 681, 686, 689, 444, 666, 665; 73/61.43, 304 C

(56) References Cited

U.S. PATENT DOCUMENTS

| | | | | |
|---|---|---|---|---|
| 4,470,300 A | * | 9/1984 | Kobayashi | 324/681 X |
| 4,947,689 A | * | 8/1990 | Hochstein | 73/304 C |
| 5,612,622 A | * | 3/1997 | Goldman et al. | 324/444 |
| 5,790,422 A | * | 8/1998 | Power et al. | 73/304 C X |
| 5,824,889 A | | 10/1998 | Park et al. | 73/116 |
| 5,900,810 A | | 5/1999 | Park et al. | 340/450.3 |
| 5,907,278 A | | 5/1999 | Park et al. | 340/450.3 |
| 5,929,754 A | | 7/1999 | Park et al. | 340/439 |

* cited by examiner

Primary Examiner—Safet Metjahic
Assistant Examiner—T R Sundaram
(74) Attorney, Agent, or Firm—Oppenheimer Wolff & Donnelly LLP

(57) ABSTRACT

A capacitive sensor is employed to measure the dielectric constant of miscible liquids, and thereby determine the relative concentration of the two liquids. Further, a feedback circuit may be provided to change the operation of the system in accordance with the relative concentration of the liquids. Further, circuit arrangements may be provided to adjust the sensitivity and offset of the electrical circuit included in the system to match the output of the sensor with the dielectric constants being measured.

17 Claims, 3 Drawing Sheets

US 6,351,132 B1

MISCIBLE LIQUID CAPACITIVE SENSING SYSTEM

FIELD OF THE INVENTION

This invention relates to capacitive liquid sensing and analysis systems.

BACKGROUND OF THE INVENTION

When two miscible fluids are mixed it is often desirable to determine the relative amount of each fluid which is present. In the case of coolant, for example, where alcohol or ethylene glycol is mixed with water, the freezing point of the liquid depends on the relative amounts of the two liquids. The relative amounts of the two liquids may be determined by using a density measuring device or hydrometer, for example, when coolants are involved so that the freezing point of the liquids may be ascertained.

However, known techniques, such as the use of a hydrometer, are not always convenient or readily compatible with electrical monitoring systems.

The disclosure of U.S. Pat. No. 5,824,389 is also noted. However, this patent does not relate to miscible liquids, but to the deterioration of a single liquid, or to the presence of an immiscible contaminant, such as water present in oil.

SUMMARY OF THE INVENTION

It is therefore an object of the invention to provide a simple electrical sensor for determining the relative concentration of miscible liquids, with such sensor being compatible with electronic systems such as feedback and control systems.

In accordance with one illustrative system, the relative concentration of two miscible liquids in a tank or other container may be determined by a capacitive sensor. With the dielectric constant of one fluid being different from the dielectric constant of the other fluid, the sensor and its associated circuitry have offset and gain control arrangements so that the electrical signal output of the sensor has a range extending linearly from a low output value when the dielectric constant of the mixture is equal to that of one of the liquids, up to a maximum when the dielectric constant of the liquid approaches that of the other of the liquids.

A feedback circuit may be provided to change the operation of the system in accordance with the relative concentrations of the liquids. In one illustrative example, the two liquids may be mixed in a tank, and electromagnetically actuated valves from two sources of liquids may be actuated selectively to keep the concentration in the tank at the desired proportions.

Feedback circuits controlling other operating parameters may also be used. For example, in the case of antifreeze, a heater may be employed to prevent temperatures from dropping below the freezing temperature of the coolant.

Other objects, features and advantages of the invention will become apparent from a consideration of the following detailed description and from the accompanying drawings.

DETAILED DESCRIPTION OF PREFERRED EMBODIMENTS

Figure 1:
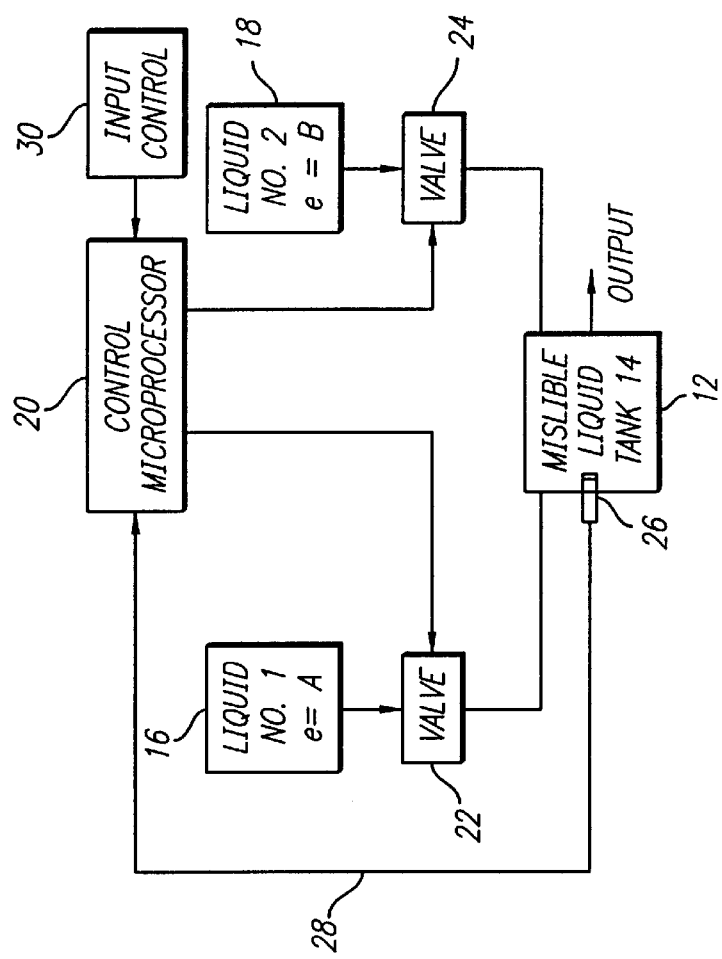
FIG. 1 is a block diagram of a system illustrating the principles of the present invention.

Referring more particularly to the drawings, FIG. 1 shows a tank 12 for containing miscible liquids 14. Sources of a liquid 16 and another liquid 18 having different dielectric constants, are indicated by the blocks 16 and 18. A microprocessor and controller 20 is operative to control the concentration of the miscible liquids 14 in tank 12, by the operation of electromagnetic valves 22 and 24. A capacitive sensor 26 provides an output signal on lead 28 indicating the dielectric constant and/or the relative concentration of the miscible liquids in tank 12.

Instructions as to the desired concentration of the miscible liquids is provided by the input control 30 which is applied to the microprocessor controller 20. The input control 30 indicates the desired concentration of the miscible liquids 14 in tank 12, and the capacitive sensor 26 provides an output signal on lead 28 indicating to the controller 20 what the actual relative concentration of the miscible liquids is at any given time. Based on these inputs to the controller 20, the valves 22 and/or 24 are operated to control the flow of the two liquids from the sources 16 and 18 into the tank 12.

Figure 2:
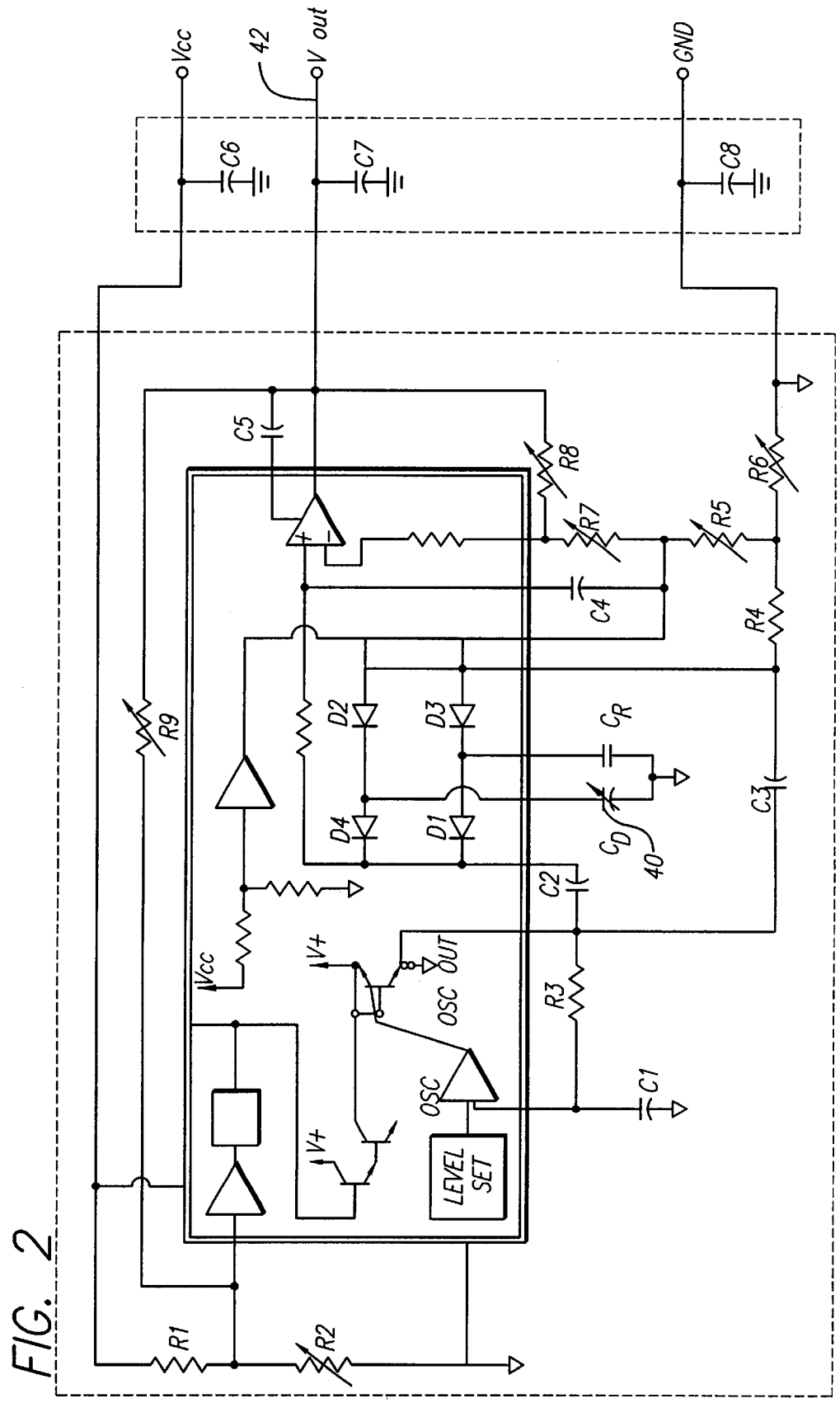
FIG. 2 is a circuit diagram of a circuit providing a variable output voltage, with variations in a sensed capacitance value.

Attention will now be directed to FIG. 2 of the drawings in which the circuit diagram for the sensor is shown. From an overall standpoint relative to FIG. 2, it may be noted that the power supply input to the circuit is indicated at $V_{cc}$ at several points in the diagram. The variable capacitance sensing capacitor is indicated at $C_D$, otherwise identified by reference numeral 40. As the capacitance 40 varies over the range of dielectric values of the two miscible liquids of FIG. 1, the output at lead 42 at the right-hand side of the diagram varies from 0.5 volts to 4.5 volts. The operation of this type of circuit is disclosed in some detail in U.S. Pat. No. 5,824,889, so the details of the complete mode of operation of the circuit will not be developed in detail in this specification.

Figure 3:
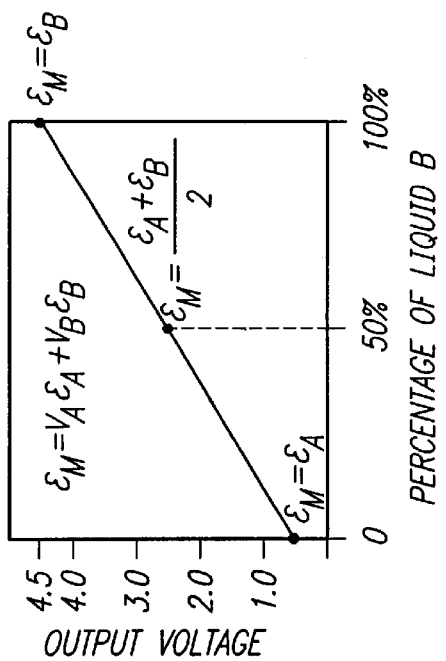
FIG. 3 is a plot of output voltage versus dielectric constant or the relative percentage or concentration of two miscible liquids.

In general it is noted that the output at lead 42 varies as shown in FIG. 3 from 0.5 volts when the dielectric constant is equal to that of the liquid designated "A" up to 4.5 volts, when the dielectric constant of the miscible liquid is equal to that of the liquid designated "B". In order to vary the offset of the circuit so that the range of the output corresponds to the widely different liquids which may be involved, the offset control variable resistors R5 and R6 may be adjusted. Further, to change the sensitivity of the circuit in the desired range, the resistors R7 and R8 may be adjusted. In some cases, the output characteristic may be concave or convex and, in order to compensate for this non-linearity, the resistors R2 or R9 may be adjusted. Accordingly, with the foregoing adjustments, the circuit of FIG. 2 provides the output characteristics as shown in FIG. 3, with the full scale reading of the output from the circuit of FIG. 2 corresponding to the dielectric constant of one of the two input fluids, while the 0.5 volt reading corresponds to the dielectric constant of the other of the input liquids.

FIG. 3 shows the output of the circuit of FIG. 2 over various concentrations of the two input liquids A and B. This output voltage is indicated by the characteristic 52; and the point 54 represents a half-and-half concentration, where the dielectric constant E is equal to $E_A + E_B \div 2$.

Figure 4:
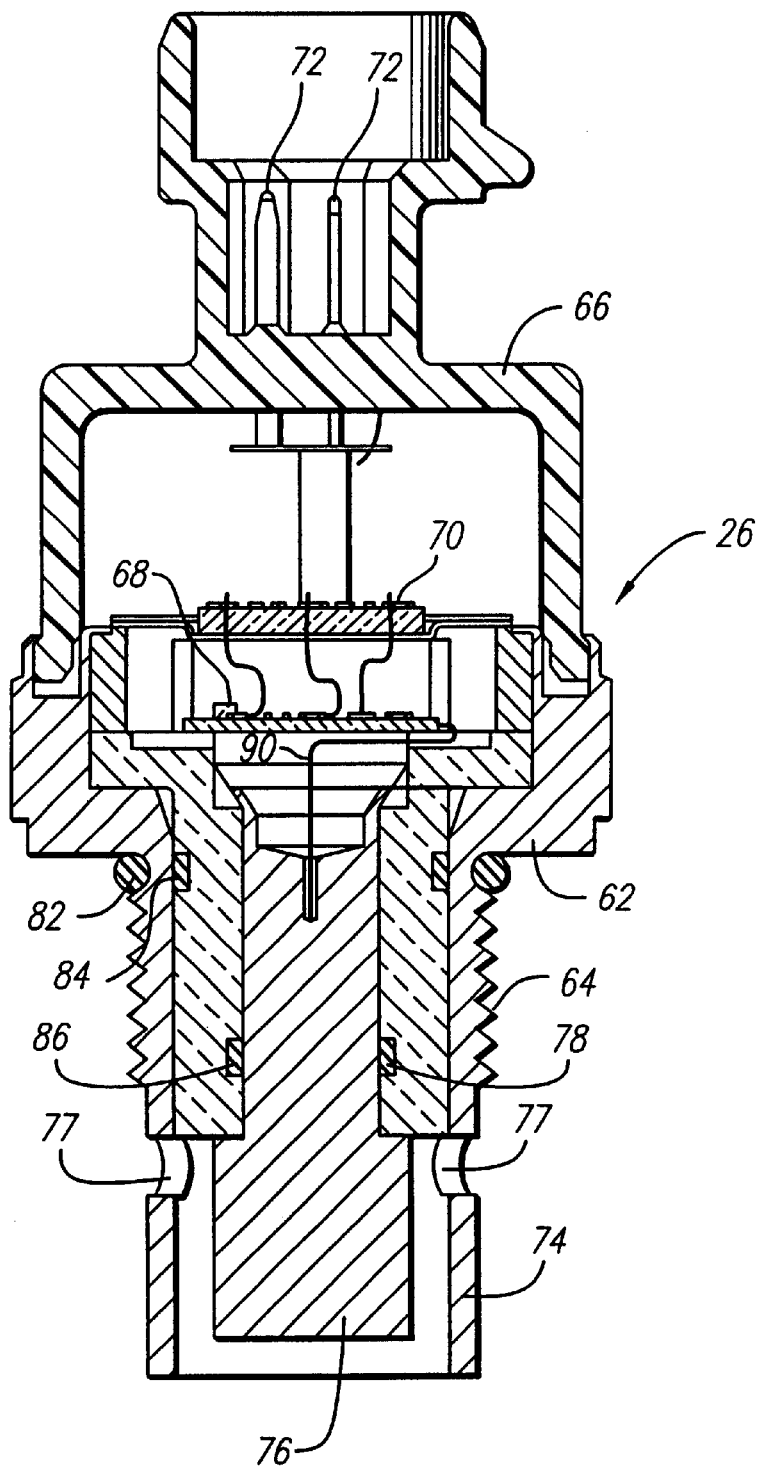
FIG. 4 is a capacitive sensor for providing a variable output depending on the dielectric constant of liquids which are being sensed.

FIG. 4 shows one embodiment which could be employed to implement the sensor shown at 26 in FIG. 1. More particularly, the sensor 26 of FIG. 4 includes the outer metallic housing 62, with threads 64 for holding the sensor into a tank such as the tank 12 of FIG. 1. The upper housing 66 may be made of high strength plastic, and encloses the hybrid circuit 68 forming the greater part of the circuit of FIG. 2, and the feed-through capacitors on the circuit board 70. The output terminal pins 72 bring energization power to the hybrid assembly and also couple the output from the lead 42 of FIG. 2 to an external circuit such as the feedback circuit of FIG. 1.

The cylindrical surface 74 at the lower end of the housing 62 in the showing of FIG. 4 constitutes one electrode of the variable capacitance, and the central metallic electrode 76 constitutes the other electrode of the sensor. The openings 77 facilitate free flow of the miscible liquids between the spaced electrodes. Incidentally, the housing 62 and the electrode 76 are preferably made of stainless steel, but may be made of other conductive material which will not react with the liquids which are being sensed. Between the electrode 76 and the housing 64 is an insulating plastic spacer 78. Suitable seals 82, 84 and 86 are provided to protect the electronics 68 and 70 from the liquids being sensed and measured. Incidentally, the outer electrode 74 is at ground potential, while the electrode 76 is coupled to the hybrid assembly 68, and to the circuit of FIG. 2 by the lead 90. To prevent the buildup of material on the electrodes, they may be coated with a low friction coating, such as a silicone based outer coating or layer.

It is noted in passing that the dielectric constants of liquids vary widely. In this regard, some commonly known fluids have the following approximate dielectric constants: (1) automotive motor oil: from about 1.6 to 3.2 depending on brand and age; (2) water—87.5; (3) diesel oil—2.0; (4) methanol—60; (5) ethylene glycol—37. Accordingly, the offset and gain arrangements mentioned hereinabove are very useful in accommodating a wide range of miscible liquids, where both the values of the dielectric constants and the differences between the dielectric constants vary over wide ranges.

It is to be understood that the foregoing description and the associated drawings are merely illustrative of one embodiment of the invention. By way of example and not of limitation, other types of capacitive sensors may be employed. Also, in addition to maintaining the concentration of the miscible liquids at a desired level, other feedback systems, such as a system involving optimal combustion conditions for miscible fuels, for specific example, may be controlled in accordance with the sensed composition of the miscible fluids. The capacitive sensor may be provided with parallel plates rather than concentric cylindrical electrodes, and digital output signals may be developed to numerically represent the varying composition of the liquids, instead of the analog output signals provided by the circuit of FIG. 2; and such circuitry including an analog-to-digital converter could be located within or external to the sensor of FIG. 4. Accordingly, the present invention is not limited the specific embodiments shown and described herein.

What is claimed is:

1. A sensing and control system comprising:
   a container;
   first and second miscible liquids in said container, said liquids having significantly different first and second dielectric constants, respectively;
   a capacitive sensor mounted to extend into said container; said sensor having spaced electrodes exposed to said liquids, wherein the capacitance between said electrodes varies with the dielectric constant of said miscible liquids, and the concentration thereof;
   said sensor having an electrical output which varies with the sensed capacitance;
   said system including adjustable operational controls for varying flow conditions of said liquids into the container; and
   feedback circuitry coupled to said sensor for varying said adjustable operational controls in accordance with the output of said sensor.

2. A system as defined in claim 1 wherein said sensor is mounted in said container near the bottom thereof so that it is normally submerged in said liquids.

3. A capacitive sensing system comprising:
   a tank;
   first and second miscible liquids in said tank, said liquids having significantly different first and second dielectric constants, respectively;
   a capacitive sensor mounted to extend into said tank, said sensor having spaced electrodes to said liquids, wherein the capacitance between said electrodes varies with the dielectric constant of said miscible liquids, and the concentration thereof;
   said sensor having an electrical output extending over a predetermined range;
   said sensor including arrangements for adjusting the offset and the gain of said sensor so that varying concentrations of said miscible liquids correspond substantially to the range of said sensor;
   feedback circuitry coupled to said sensor for varying operating conditions of said system in accordance with the output of said sensor; and
   a source of one of said liquids, and an electrically operated valve coupling said source to said tank, a second source of the other of said liquids and an electrically operated valve coupling said second source to said tank, and said feedback circuitry being coupled to control said valves to provide the desired concentration of said liquids.

4. A capacitive sensing system comprising:
   a container;
   first and second miscible liquids in said container, said liquids having significantly different first and second dielectric constants, respectively;
   a capacitive sensor mounted to extend into said container; said sensor having spaced electrodes exposed to said liquids, wherein the capacitance between said electrodes varies with the dielectric constant of said miscible liquids, and the concentration thereof;
   said sensor having an electrical output which varies with the sensed capacitance;
   feedback circuitry coupled to said sensor for varying operating conditions of said system in accordance with the output of said sensor; and
   a source of one of said liquids, and an electrically operated valve coupling said source to said tank, a second source of the other of said liquids and an electrically operated valve coupling said second source to said container, and said feedback circuitry being coupled to control said valves to provide the desired concentration of said liquids.

5. A capacitive sensing system comprising:
   a container;
   first and second miscible liquids in said container, said liquids having significantly different first and second dielectric constants, respectively;

a capacitive sensor mounted to extend into said container; said sensor having spaced electrodes exposed to said liquids, wherein the capacitance between said electrodes varies with the dielectric constant of said liquids, and the concentration thereof;

said sensor including electronic circuitry providing a normal electrical output which varies with the sensed capacitance;

said system further including at least one variable liquid control component; and feedback arrangements coupled to said sensor for varying the operating conditions of said system by changing the state of said liquid control component in accordance with the output of said sensor.

6. A capacitive sensing system comprising:

a container;

first and second miscible liquids in said container, said liquids having significantly different first and second dielectric constants, respectively;

a capacitive sensor mounted to extend into said container; said sensor having spaced electrodes exposed to said liquids, wherein the capacitance between said electrodes varies with the dielectric constant of said liquids, and the concentration thereof;

said sensor including electronic circuitry providing a normal electrical output which varies with the sensed capacitance;

said system further including at least one variable physical component for variably controlling said liquids, in addition to said electronic circuitry; and feedback arrangements coupled to said sensor for varying the operating conditions of said system by changing the state of said physical component in accordance with the output of said sensor.

7. A system as defined in claim 6 wherein said variable physical component includes at least one valve.

8. A capacitive sensor system as defined in claim 1 including a source of one of said liquids, and an electrically operated valve coupling said source to said container, a second source of the other of said liquids and an electrically operated valve coupling said second source to said container, and said feedback circuitry being coupled to control said valves to provide the desired concentration of said liquids.

9. A capacitive sensor system as defined in claim 1 wherein said sensor is mounted in said container near the bottom thereof so that it is normally submerged in said liquid.

10. A capacitive sensor system as defined in claim 1 wherein said sensor includes a threaded housing for securing said sensor to said housing, with a pair of closely spaced capacitive plates extending into said container.

11. A capacitive sensor system as defined in claim 10 wherein said capacitive plates are concentric.

12. A capacitive sensor system as defined in claim 10 wherein said housing includes electronic circuitry for converting variations in the capacitance sensed by said plates into corresponding variations in output signal from said circuitry.

13. A capacitive sensor system as defined in claim 1 wherein said system includes a microprocessor coupled to receive signals from said sensor and to implement desired operating conditions of the system.

14. A capacitive sensor system as defined in claim 4 wherein the output of said sensor normally extends over a predetermined range, and wherein said system includes circuitry associated with said sensor for adjusting the offset and the gain of said sensor so that varying concentrations of said miscible liquids correspond substantially to the range of said sensor.

15. A capacitive sensor system as defined in claim 4 wherein said sensor includes a threaded housing for securing said sensor to said housing, with a pair of closely spaced capacitive plates extending into said container.

16. A capacitive sensor system as defined in claim 15 wherein said capacitive plates are concentric.

17. A capacitive sensor system as defined in claim 4 wherein said system includes a microprocessor coupled to receive signals from said sensor and to implement desired operating conditions of the system.

* * * * *